United States Patent
Klimberg et al.

(10) Patent No.: US 6,714,808 B2
(45) Date of Patent: Mar. 30, 2004

(54) METHOD FOR DETECTING AND EXCISING NONPALPABLE LESIONS

(75) Inventors: V. Suzanne Klimberg, Little Rock, AR (US); Steven E. Harms, Little Rock, AR (US); Sohelia Korourian, Little Rock, AR (US)

(73) Assignee: University of Arkansas, Little Rock, AR (US)

( * ) Notice: Subject to any disclaimer, the term of this patent is extended or adjusted under 35 U.S.C. 154(b) by 167 days.

(21) Appl. No.: 09/970,456

(22) Filed: Oct. 3, 2001

(65) Prior Publication Data

US 2002/0052545 A1 May 2, 2002

Related U.S. Application Data

(60) Provisional application No. 60/237,671, filed on Oct. 3, 2000.

(51) Int. Cl.⁷ ............................................... A61B 5/055
(52) U.S. Cl. ....................................... 600/411; 600/437
(58) Field of Search ................................ 600/411, 437; 602/43, 52

(56) References Cited

U.S. PATENT DOCUMENTS

| | | | |
|---|---|---|---|
| 4,014,650 A | * 3/1977 | Sigelmann | 436/108 |
| 4,469,098 A | 9/1984 | Davi | |
| 5,193,106 A | * 3/1993 | DeSena | 378/163 |
| 5,270,030 A | * 12/1993 | Vogel et al. | 424/1.69 |
| 5,614,204 A | * 3/1997 | Cochrum | 424/423 |
| 5,789,921 A | 8/1998 | Albert et al. | |

OTHER PUBLICATIONS

Kass, R. et al. Efficacy of Hematoma–directed Ultrasound Gulded (HUG) Excision after Vacuum Assisted Core Biopsy, poster presentation at the 4th Annual American Society of Breast Surgeons, Atlanta GA, May 1–4, 2003.

Kass, R. et al. Clip Migration: Implication in Positive Margin Status After Needle Localization Breast Biopsy, Oral presentation at the American Society of Breast Surgeons, Boston MA, Apr. 24–27, 2002.

Kass, R., et al., Clip migration in stereotactic biopsy, Am. J. Surgery, 2002, 184:325–331.

Smith, L.F., et al. Introperative localization after sterotatic breast biopsy without a needle, *The Americal Journal of Surgery* 2001; 182(6): 584–589.

(List continued on next page.)

*Primary Examiner*—Dennis W. Ruhl
*Assistant Examiner*—Runa Shah Qaderi
(74) *Attorney, Agent, or Firm*—Kilpatrick Stockton LLP; Charles Calkins; Cynthia B. Rothschild

(57) ABSTRACT

A novel method of hematoma-directed ultrasound guided excisional breast biopsy is disclosed. In one aspect of the inventon, the hematoma is produced by an injection of the patient's own blood into a pre-selected area to target a lesion. Detection of the targeted lesion and hematoma is achieved with MRI. In a second aspect of the invention, the hematoma is produced by stereotactic core needle breast biopsy in a pre-selected area, and the targeted lesion and hematoma are detected using intraoperative ultrasound. The method avoids many of the disadvantages associated with traditional needle localized breast biopsy. The method can also be used to guide the excision of lesions visualized by MRI, ultrasound, mammography, PET scanning, and scintimammography. The method may be used in any organ and, in particular, the breast.

24 Claims, 11 Drawing Sheets

OTHER PUBLICATIONS

Smith, L.F., et al. Intraoperative ultrasound guided breast biopsy, presented at the Southwestern Surgical Conference, Cancun, Mexico, Apr. 29–May 2, 2001.

Bassett, L et al. Stereotactic core needle biopsy of the breast: a report of the joint task force of the American College of Radiology, American College of Surgeons, and College of American Pathologists. *CA Cancer J Clin.* 1997;47(3):171–90.

Brenner, RJ et al. Stereotactic core–needle breast biopsy: a multi–institutional prospective trial. *Radiology.* 2001;218(3):866–72.

Burns, RP Image–guided breast biopsy. *Am J Surg.* 1997;173:9–11.

Cox, CE et al. Touch preparation cytology of breast lumpectomy margins with histologic correlation. *Archives of Surgery* 1991;126:490–493.

Di Giorgio, A et al. A. Ultrasound guided excisional biopsy of non–palpable breast lesions: technique and preliminary results. *European Journal of Surgery* 1998;164:819–824.

Fuhrman, GM et al. Image–guided core–needle breast biopsy is an accurate technique to evaluate patients with nonpalpable imaging abnormalities. *Ann Surg.* 1998;227(6):932–39.

Gennari, R et al. Use of technetium–99m–labeled colloid albumin for preoperative and intraoperative localization of nonpalpable breast lesions. *J Am Coll Surg* 2000;190:692–699.

Harlow, SP et al. Intraoperative ultrasound localization to guide surgical excision of nonpalpable breast carcinoma. *Journal of the American College of Surgeons* 1999;189:241–246.

Hasselgren, PO et al. Breast Biopsy with needle localization: accuracy of specimen x–ray and management of missed lesions. *Surgery* 1993; 114:836–42.

Homer, MJ et al. Prebiopsy needle localization: methods, problems, and expected results. *Radiologic Clinics of North America* 1992; 30(1):139–153.

Howisey, RL et al. A comparison of medicare reimbursement and results for various imaging–guided breast biopsy techniques. *Am J Surg.* 1997;173:395–398.

Israel PS et al, *Stereotactic needle biopsy for occult breast lesions: a minimally invasive alternative*, Am Surg 61:87–91 (1995).

Klimberg, VS et al. Use of touch preps for diagnosis and surgical margins in breast cancer. *Annals of Surgical Oncology* 1998; 5(3):220–226.

Krag, D et al. The sentinel node in breast cancer: a multicenter validation study. *New Engl J Med* 1998;339:941–946.

Lee, CH et al. Cost–effectiveness of stereotactic core needle biopsy: analysis by means of mammographic findings. *Radiology.* 1997;202:849–854.

Liberman, L et al. Impact of stereotaxic core breast biopsy on cost of diagnosis. *Radiology.* 1995;195:633–637.

Luini, A et al. Comparison of radioguided excision with wire localization of occult breast lesions. *Br J Surg* 1999;86(4):522–25.

Meyer, JE et al. Large–core needle biopsy of nonpalpable breast lesions. *JAMA* 1999;281(17):1638–41.

Parker, SH et al. Stereotactic breast biopsy with a biopsy gun. *Radiology* 1990;176:741–47.

Pettine, S et al. Stereotactic breast biopsy is accurate, minimally invasive, and cost effective. *Am J Surg.* 1996;171:474–76.

Rahusen, FD et al. Ultrasound–guided lumpectomy of nonpalpable breast cancers: a feasibility study looking at the accuracy of obtained margins. *Journal of Surgical Oncology* 1999;72:72–76.

Rissanen, TJ et al. Wire localized biopsy of breast lesions: a review of 425 cases found in screening or clinical mammography. *Clinical Radiology* 1993; 47:14–22.

Schwartz, GF et al. Ultrasonography: an alternative to x–ray–guided needle localization of nonpalpable breast masses. *Surgery* 1988;104:870–873.

Smith, LF et al. Intraoperative ultrasound–guided breast biopsy. *Am J Surg* 2000;180:419–423.

Smith, L et al. Hematoma–directed ultrasound–guided breast biopsy. *Ann Surg* 2001;233(5):669–675.

Snider, HC et al. Intraoperative ultrasound localization of nonpalpable breast lesions. *Annals of Surgical Oncology* 1999; 6(3):308–314.

Staren, ED et al. Surgeon–performed ultrasound: breast ultrasound. *Surgical Clinics of North America* 1998;78(2):219–235.

Velanovich, V et al. Comparison of mammographically guided breast biopsy techniques. *Ann Surg.* 1999;229(5):625–33.

Wilson, M et al. Non–invasive ultrasound localization of impalpable breast lesions. *Clinical Radiology* 1993;47:337–338.

Yim, JH et al. Mammographically detected breast cancer—benefits of stereotactic cores versus wire localization breast biopsy. *Ann Surg.* 1996;223:688–700.

\* cited by examiner

METHOD FOR DETECTING AND EXCISING NONPALPABLE LESIONS

CROSS-REFERENCE TO RELATED APPLICATION

This application claims the benefit of U.S. Provisional Application Ser. No. 60/237,671 filed Oct. 3, 2000, which is incorporated by reference in its entirety.

BACKGROUND OF THE INVENTION

The present invention relates generally to a method for detecting and excising nonpalpable lesions and, more particularly, to a hematoma-directed ultrasound guided excisional breast biopsy.

Increased screening mammography has led to over 1,000,000 breast biopsies performed yearly in the United States. An increasing number of these biopsies are for nonpalpable mammographic abnormalities and less than one-third are visible with ultrasound. Available options for biopsy of these mammographic abnormalities have included needle localization excisional breast biopsy (NLBB) or percutaneous stereotactic core needle breast biopsy (SCNBB).

Magnetic resonance imaging (MRI) of the breast has allowed for the visualization of lesions previously undetected by mammography. Despite the availability of MRI guided needle localization techniques at medical institutions, the patient is still subjected to the disadvantages and complications inherent to this method of biopsy. Although NLBB most often results in the successful removal of the targeted lesion in mammographically detected lesions, the miss rate varies from 0 to 22% [Snider HC et al., Intraoperative ultrasound localization of nonpalpable breast lesions, *Ann Surg Oncol* 6(3):308–314 (1999); Rissanen T J et al., Wire localized biopsy of breast lesions: a review of 425 cases found in screening or clinical mammography, *Clin Radiol* 47:14–22 (1993); Hasselgren P O et al., Breast biopsy with needle localization: accuracy of specimen x-ray and management of missed lesions, *Surgery* 114:836–42 (1993); and Homer M J et al., Prebiopsy needle localization: methods, problems, and expected results, *Radiol Clin North Am* 30(1):139–153 (1992)]. The rate is unknown for MRI NLBB, where even thinner wires are used and where the technology is not universally available.

Specimen mammography is used to confirm excision of the targeted lesion after NLBB. In contrast, "specimen MRI" is not possible because MRI requires living tissue with a blood supply to demonstrate areas of enhancement of the targeted lesion. Confirmation of removal requires a separate MRI of the remaining breast tissue in the patient on a separate day.

Although NLBB is considered the "standard" for removal of mammographically-detected, nonpalpable breast lesions, disadvantages include the possibility of significant vasovagal reactions which occur in 10 to 20% of patients, the discomfort of the wire, and the possibility of wire transection or migration [Rissanen T J et al, Wire localized biopsy of breast lesions: a review of 425 cases found in screening or clinical mammography, *Clin Radiol* 47:14–22 (1993); and Homer M J et al., Prebiopsy needle localization: methods, problems, and expected results, *Radiol Clin North Am* 30(1):139–153 (1992)].

The proven accuracy of SCNBB as well a better rate of margin clearance when the diagnosis of cancer has been established prior to definitive procedure has influenced many surgeons in favor of SCNBB [Yim J H et al., Mammographically detected breast cancer-benefits of stereotactic cores versus wire localization breast biopsy, *Ann Surg.* 223:688–700 (1996); Israel P S et al., Stereotactic needle biopsy for occult breast lesions: a minimally invasive alternative, *Am Surg* 61:87–91 (1995); Velanovich F et al., Comparison of mammographically guided breast biopsy techniques, *Ann Surg* 229(5):625–33 (1999); Fuhrman G M et al., Image-guided core-needle breast biopsy is an accurate technique to evaluate patients with nonpalpable imaging abnormalities, *Ann Surg.* 227(6):932–39 (1998); and Meyer J E et al., Large-core needle biopsy of nonpalpable breast lesions *JAMA* 281(17):1638–41 (1999)]. However, when the results of SCNBB require further evaluation, NLBB has been the only tool available to the surgeon.

There, thus, remains a need to develop an alternative method that can be used to excise nonpalpable lesions and, at the same time, provide a greater comfort level for the patient.

SUMMARY OF THE INVENTION

The present invention is directed to a hemotoma-directed ultrasound guided method for detecting and excising nonpalpable lesions in a patient. The method can be used not only to localize a MRI-detected lesion, but also to outline the targeted lesion for complete excision and to obtain margins. The method of the present invention overcomes many of the disadvantages associated with traditional NLBB, for example, discomfort, significant vasovagal reactions (i.e., vomiting, nausea, fainting), frequent delay of surgery, wire transection or migration, significant miss rate, and additional imaging to confirm lesion removal.

Twenty patients with nonpalpable breast lesions detected by MRI only were enrolled in a single institution trial. A hematoma comprising about 2–5 ml of the patient's own blood was injected into the breast to target the nonpalpable lesion. Intraoperative ultrasound of the hematoma was used to direct the excisional biopsy.

Ninety-five percent of the lesions detected by MRI were successfully localized by hematoma injection. All of the hematomas used to recognize targeted lesions were successfully identified at surgery by ultrasound and then removed without complication. Eight (40%) of the lesions were malignant with an average tumor size of 12±6 mm (range 4–25 mm). The remaining 12 lesions (60%) comprised papillomas, sclerosing adenosis, radial scars, fibroadenomas, and areas of a typical ductal hyperplasia.

The hematoma can be created by a blood injection using the patient's own blood or naturally by stereotactic core needle biopsy (SCNBB). The hematoma resulting from SCNBB can be used to localize the SCNBB site with intraoperative ultrasound for excision.

20 patients had SCNBB followed by intraoperative ultrasound-guided excision. The previous SCNB site in 19 patients was successfully visualized with intraoperative ultrasound and excised at surgery. One patient had successful removal of the targeted area under ultrasound guidance, but failed to show removal of the clip on the initial specimen mammogram.

The results demonstrate the effectiveness of hematoma-directed MRI-guided breast biopsy for nonpalpable lesions by blood injection and by needle biopsy using stereotactic guidance. This novel procedure is potentially more comfortable for patients than current procedures because no wire or needle is left in the breast. The procedure of the present invention is technically faster and easier because ultrasound is used to visualize directly the location of the hematoma at surgery and to confirm lesion removal in the operating room by specimen ultrasound. The hematoma can be inserted into the patient several days before the biopsy, resulting in greater flexibility in scheduling the biopsy and alleviation of the fear of wire migration that frequently occurs with NLBB.

In addition to MRI-detected lesions, it is contemplated that the method of the present invention can be used to guide the excision of lesions visualized by other modalities including mammography, PET scanning, and scintimammography.

In one aspect of the present invention, a method for detecting and excising nonpalpable lesions, comprising the steps of: (a) injecting at least one hematoma into a mammal's breast to target a nonpalpable lesion; wherein the hematoma comprises approximately 2 ml to about 5 ml of the mammal's own blood; (b) detecting the location of the targeted lesion using MRI; and thereafter (c) excising the targeted lesion. The method may further include the step of confirming the excision of the lesion by ex vivo ultrasound. The hematoma is placed in the mammal's breast for a period of about several hours to about several days before excision of the targeted lesion. The hematoma may be combined with at least one composition for injection into the mammal. The mammal may be a human or an animal. Most importantly, the method may be performed in any organ, not just the breast.

In another aspect of the invention, at least one hematoma is produced in the mammal's breast by stereotactic core needle biopsy to target a nonpalpable lesion. Detection of the targeted lesion is achieved by ultrasound followed by excision of the targeted lesion.

DETAILED DESCRIPTION OF THE INVENTION

Figures 1A, 1B:
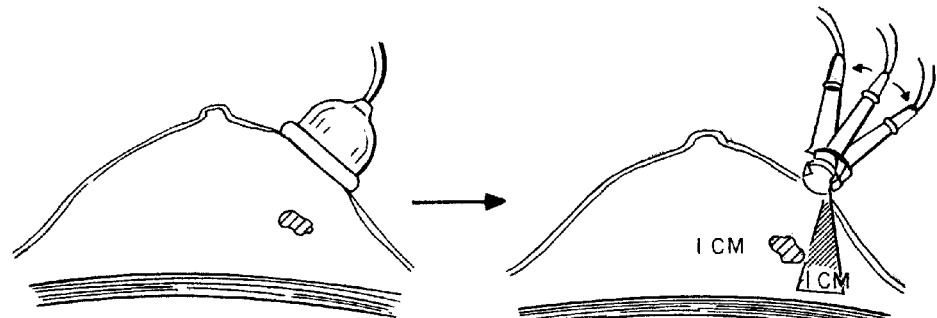
FIG. 1a illustrates an ultrasound probe over the breast lesion in craniocaudal view.
FIG. 1b illustrates an ultrasound probe tilted to show the location of one centimeter margin medial and lateral to the lesion (superiorly and inferiorly not shown). Dissection is carried straight down along the path determined by "line of sight."
Figure 1C:
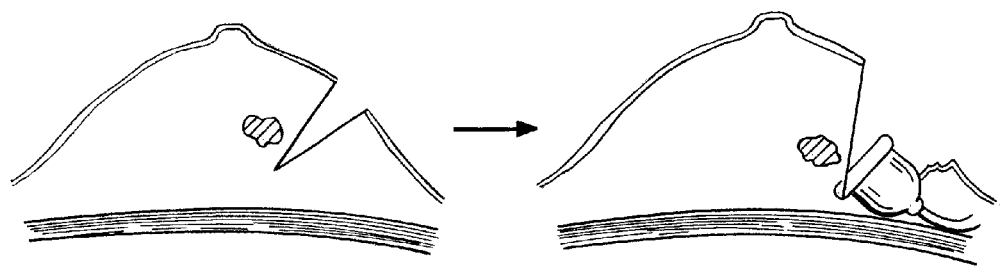
FIG. 1c illustrates a probe placed in the incision transversely to assess depth of the dissection.
Figure 1D:
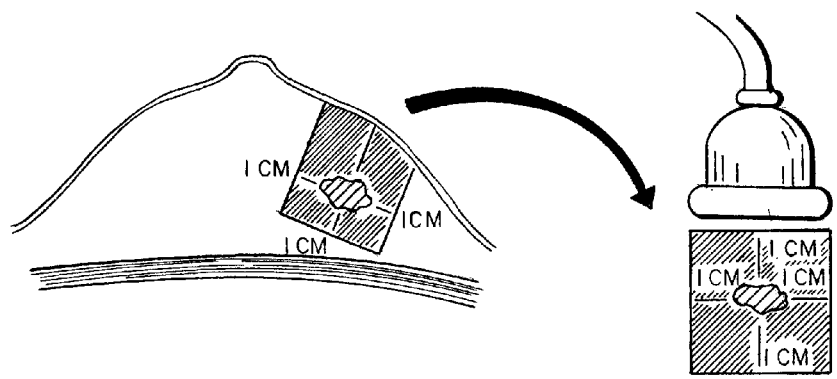
FIG. 1d illustrates tissue excised in block fashion with one centimeter margin on all sides.

I. Hematoma Produced by Blood Injection Methods

A. Patients

Twenty patients were enrolled in a single institution trial. Approval was granted by the institutional review board (IRB) and patients gave informed consent. Patients included in this study were those who had lesions that were not seen well by mammography or ultrasound, but were visualized by MRI alone. Lesions that underwent biopsy had suspicious features, including enhancement by gadolinium, spiculated masses, ring enhancement, or a clumping pattern.

B. MRI Localization Procedure

Patients were scanned using the MRI technique that utilizes a pulse sequence called RODEO (rotating delivery of excitation off-resonance). This method produces fat-suppressed images with a high signal-to-noise ratio in three-dimensional acquisition. Patients initially had noncontrast images of the breast in question, followed by an injection of gadolinium and a second MRI. The lesion was identified by increased enhancement on the postcontrast image versus the precontrast image.

C. Hematoma Injection Procedure

Before MRI scanning, approximately 2 ml to about 5 ml of blood was withdrawn from each patient, and was left to stand for at least 10 minutes. Air was incorporated into the clotted blood by manual agitation. After the initial images were obtained, a needle, either the 20-gauge E-Z-EM MRI Compatible Breast Lesion Marking System (E-Z-EM Corp, Westbury, N.Y.) or the 14-gauge Daum Coax MRI Needle (Daum Corp, Chicago, Ill.), was directed into the breast under laser guidance. A second MRI image was obtained to confirm needle placement. Then the blood was injected into the localization needle. Wires were placed through the needle in a few cases.

D. Intraoperative Ultrasound

The location of the lesion relative to the hematoma was determined from the MRI. A sterilely covered 7.5-MHz linear array transducer (Acoustic Imaging, Dornier Medical Systems, Inc., Kenneshaw, Ga.) was used to determine the precise hematoma location in the breast. The abnormality was localized in the standard longitudinal and transverse planes. After the incision was made, the transducer was placed inside the incision and the hematoma was again visualized. Dissection was carried straight down toward the chest wall using a "line of site" technique [see Krag D et al., The sentinel node in breast cancer: a multicenter validation study, *New Engl J Med* 339:941–946 (1998)]. This technique, shown in FIGS. 1a–1d, was adapted from and mimics the use of the gamma probe in sentinel lymph node surgery. The transducer was placed perpendicular to the lesion and parallel to the chest wall to assess the adequacy of the deep margin. Tissue was excised around the hematoma in a block fashion down to the ascertained depth, aiming to achieve a 1-cm margin. Ex vivo ultrasound was performed on the specimen in a basin or glove filled with water. Excision of the targeted lesion was also confirmed by direct visualization of the hematoma by ex vivo ultrasound. Wires, when present, were removed along with the specimen.

E. Pathology

Intraoperative touch preparation was performed on all six margins (anterior, posterior, medial, lateral, superior, and inferior) as described by the University of Arkansas for Medical Sciences and others [Klimberg VS et al., Use of touch preps for diagnosis and surgical margins in breast cancer, *Ann of Surg Oncol* 5(3):220–226 (1998); and Cox C E et al., Touch preparation cytology of breast lumpectomy margins with histologic correlation, *Arch Surg* 126:490–493 (1991)]. Any margins positive by touch prep were reexcised. Subsequently, the margins were inked with six different colors for the six margins. Slides were stained with hematoxylin and eosin and examined for evidence of malignancy. The specimen was serially sectioned at 5-mm intervals. Permanent margins were classified as positive pathologically if tumor cells were present at the inked margin. Hematoxylin and eosin staining was used to confirm hematoma and lesion removal.

Results

A. Patients

A total of 20 patients with an average age of 53.8 years±10 years (range 30–71) gave consent to enroll in this study. Reasons for obtaining MRI in these patients with nonpalpable lesions not seen by mammography were as follows: 1) high risk screening MRI obtained for patients enrolled in a multi-center high risk MRI protocol; 2) screening for contralateral breast cancer; 3) to determine the extent of a known cancer; 4) to rule out multicentricity; 5) for bloody nipple discharge; and 6) at the patient's request.

B. MRI Localization

Figure 2:
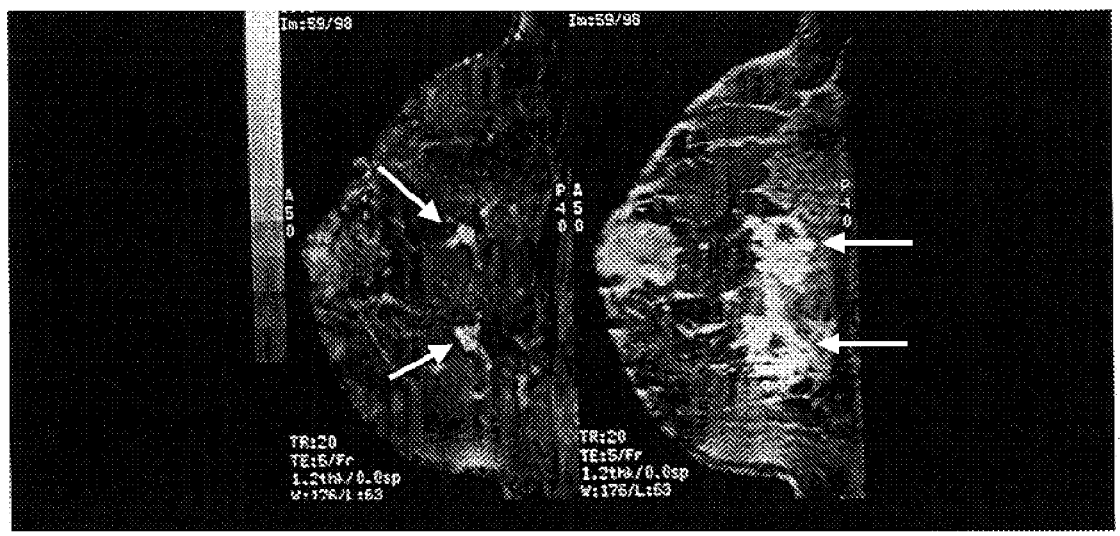
FIG. 2 represents an MRI scan showing lesions (white arrows) within the breast before hematoma injection (left image). The right MRI scan of the breast illustrates two hemotomas (white arrows).

Breast hematomas were successfully created in 19 of 20 patients in this study using about 2 to about 5 ml blood per injection site. In the remaining patient, the breast tissue was too dense to allow injection of the blood into the breast tissue, and a wire was placed through the needle used for hematoma injection. Hematomas, as shown in FIG. 2, were placed a few hours to 6 days before surgical excision of the lesion. All patients underwent subsequent surgery to the localized areas. In initial cases, wires were placed in addition to hematomas in 13 patients. In several cases, the wire was noted to have migrated distant to the hematoma and lesion.

C. Ultrasound Localization

Figure 3A:
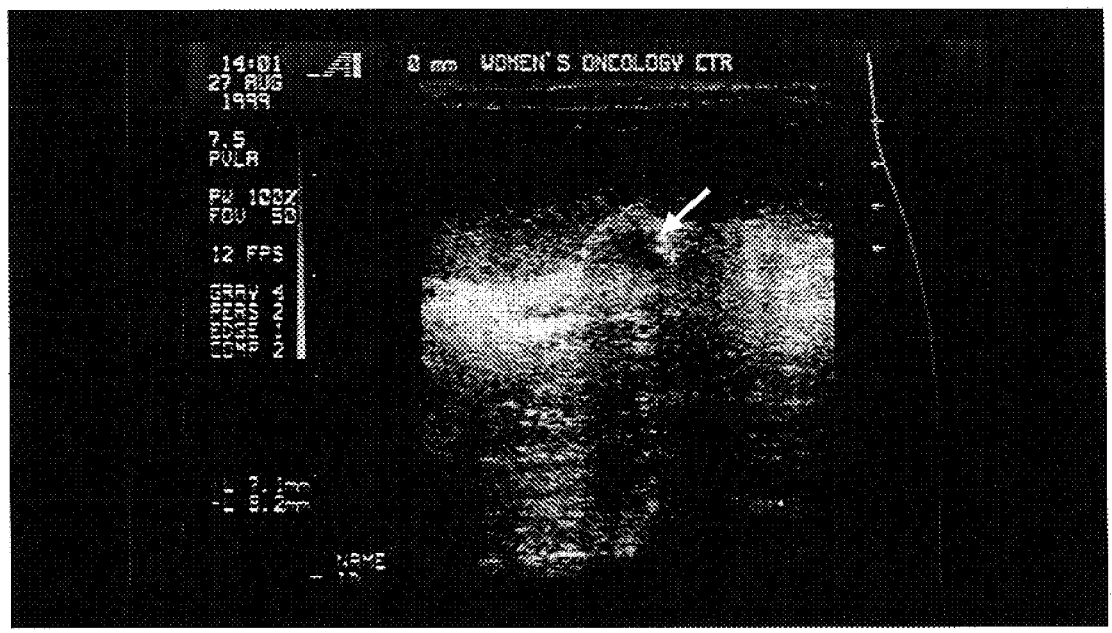
FIG. 3a represents an ultrasound image depicting a hematoma (white arrow) within the breast.
Figure 3B:
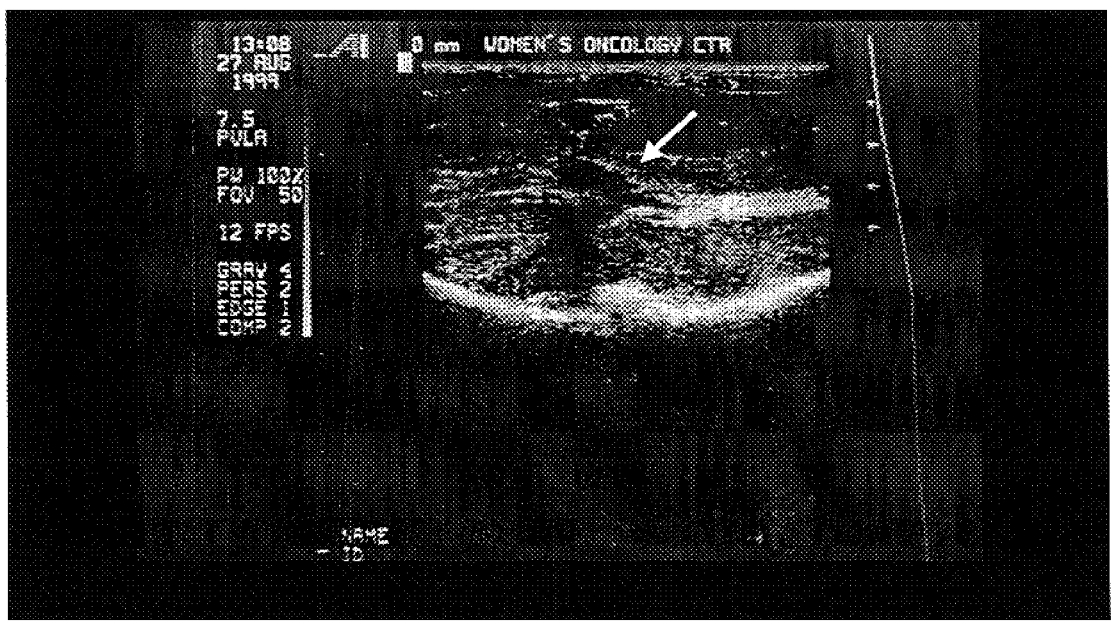
FIG. 3b represents an ex vivo ultrasound image a depicting a hematoma (white arrow) in excised breast tissue.

Ultrasound was successfully used to localize the hematomas during surgery (FIG. 3*a*) in all 19 patients where hematomas were placed. Ex vivo ultrasound or direct visualization of the hematoma, which is shown in FIG. 3*b*, confirmed removal of the hematoma or hematomas in all 19 patients.

D. Pathology

Figure 4A:
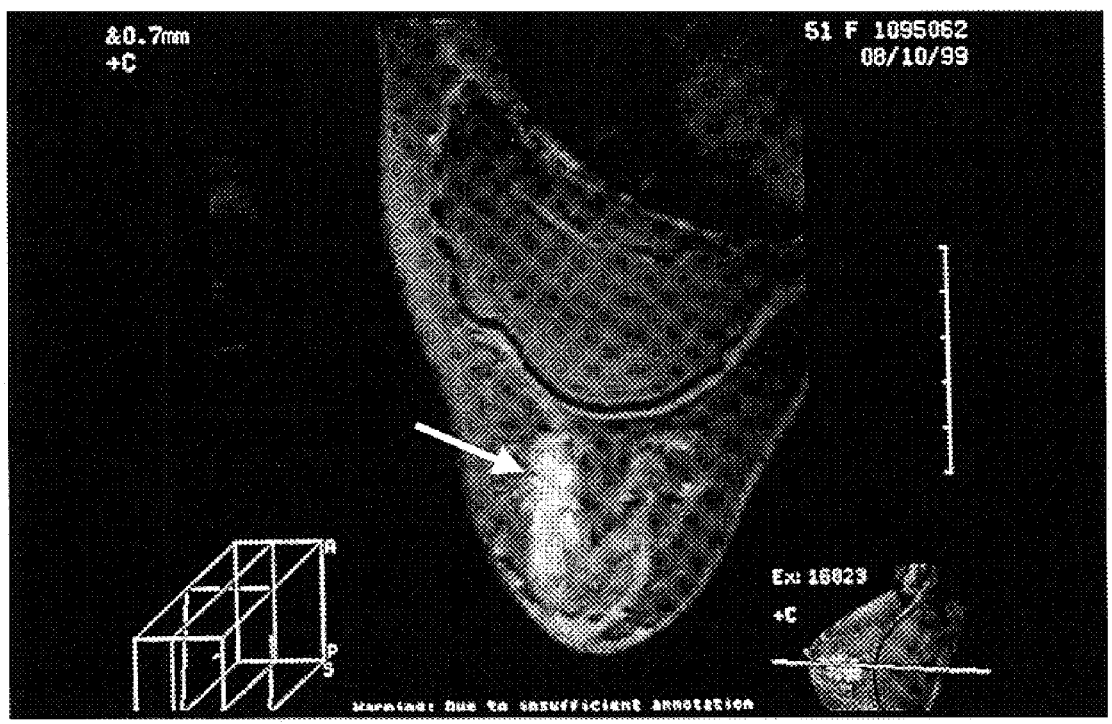
FIG. 4a represents an axial MRI image of the breast with a linear lesion extending from anterior to posterior in the breast (white arrow).
Figure 4B:
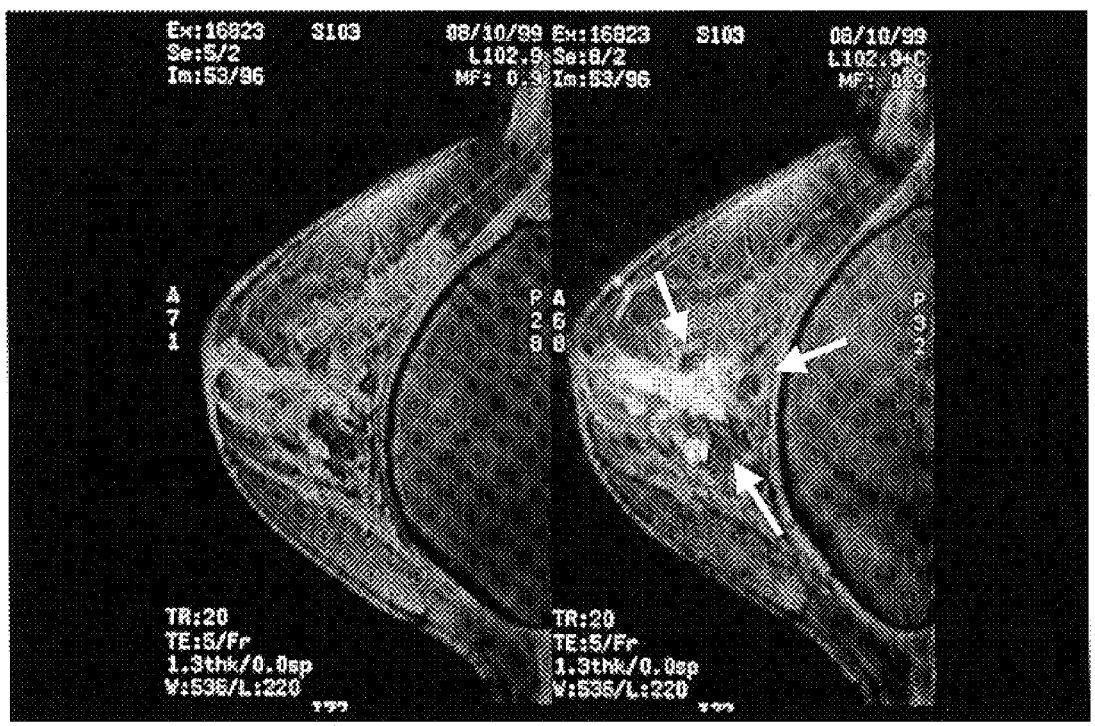
FIG. 4b represents an MRI image of the same breast in the sagittal view, demonstrating hematomas (white arrows) in position superior and inferior to the breast lesion.
Figure 5:
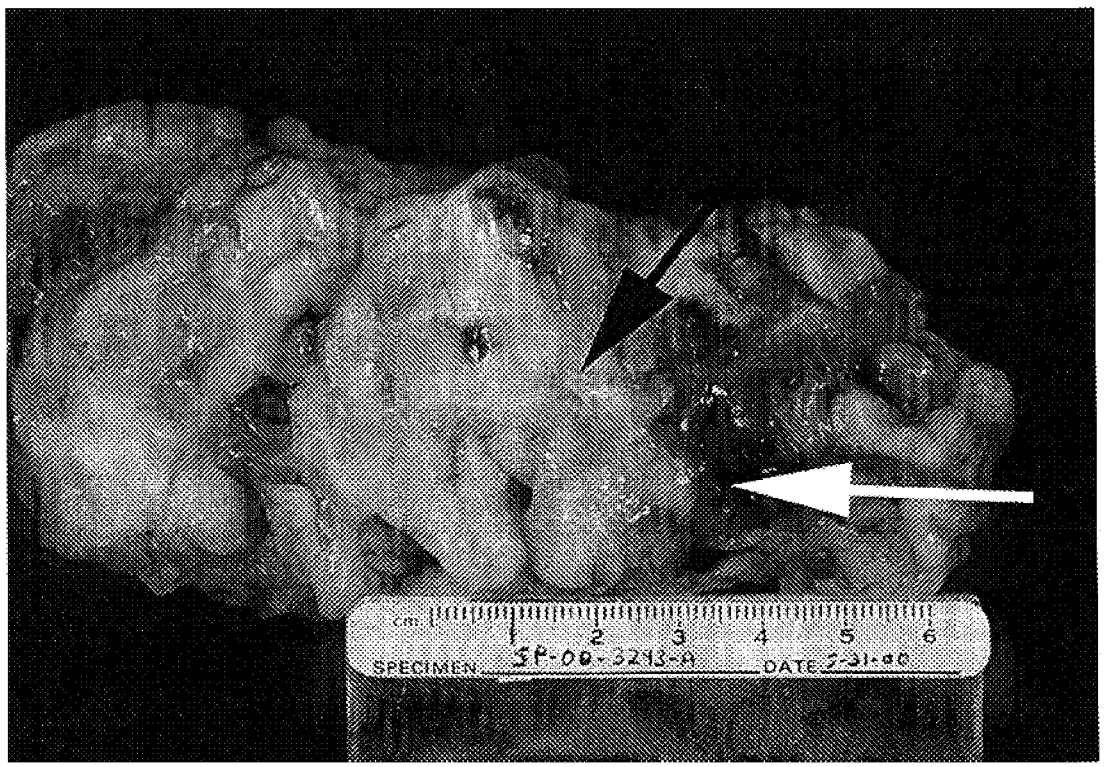
FIG. 5 illustrates a transected gross breast specimen showing breast cancer (black arrow) in close proximity to the injected hematoma (white arrow).
Figure 6:
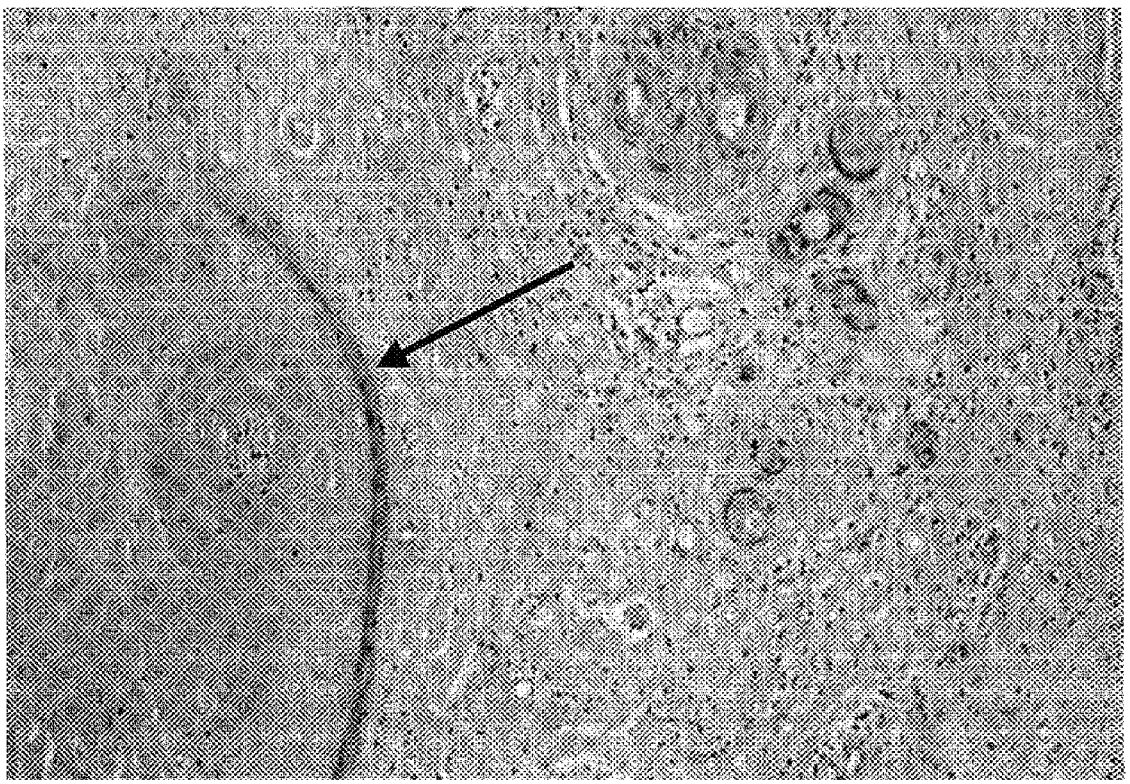
FIG. 6 illustrates a microscopic specimen showing breast carcinoma with hematoma (black arrow) at the edge of the carcinoma.

Eight (40%) of the MRI-detected lesions were malignant, with an average tumor size of 12 mm±6 mm (range 4–25). The remaining 12 lesions (60%) comprised papillomas, fibrous mastopathy, sclerosing adenosis, radial scar, fibroadenoma, and areas of atypical ductal hyperplasia. The average size of the benign lesions was 12 mm±4 mm (range 5–15). More than one hematoma was placed in the breast to outline the extent of disease in 14 patients. As shown in FIG. 4, hematomas were placed superior and inferior to the lesion to outline and guide surgical resection. In 3 patients, more than one hematoma was placed to localize more than one lesion. The hematoma which was visualized by MRI, ultrasound, and then grossly (see FIG. 5) in many cases could also be visualized microscopically to confirm lesion removal (see FIG. 6). The average closest margin was 3 mm±2 mm (range 0–7).

E. Complications

Skin necrosis developed in one patient. In another patient, an immediate postoperative hematoma developed that required evacuation. Two patients had margins that were either positive or less than 1 mm, and subsequently had completion mastectomies.

Discussion

The results of this study show the effectiveness of hematoma-localization for excisional breast biopsies in cases requiring some type of image-guided localization, in particular MRI visualized lesions. With the increasing availability of MRI for the breast, a surgeon is often faced with a dilemma on how best to perform excisional biopsy on these lesions when they cannot be visualized by any other imaging method. The University of Arkansas for Medical Sciences and other institutions have had success using the ultrasound in the operating room to excise nonpalpable lesions [Snider H C et al., Intraoperative ultrasound localization of nonpalpable breast lesions, *Ann Surg Oncol* 6(3):308–314 (1999); Smith L F et al., Intraoperative ultrasound-guided breast biopsy, *Am J Surg* 180:419–423 (2000); Staren E D et al., Surgeon-performed ultrasound: breast ultrasound, *Surg Clin North Am* 78(2):219–235 (1998); Schwartz G F et al., Ultrasonography: an alternative to x-ray-guided needle localization of nonpalpable breast masses, *Surgery* 104:870–873 (1988); Wilson M et al., Non-invasive ultrasound localization of impalpable breast lesions, *Clin Radiol* 47:337–338 (1993); Di Giorgio A et al., Ultrasound guided excision biopsy of nonpalpable breast lesions: technique and preliminary results, *Eur J Surg* 164:819–824 (1998); Rahusen F D et al., Ultrasound-guided lumpectomy of nonpalpable breast cancers: a feasibility study looking at the accuracy of obtained margins, *J Surg Oncol* 72:72–76 (1999); and Harlow S P et al., Intraoperative ultrasound localization to guide surgical excision of nonpalpable breast carcinoma, *J Am Coll Surgeons* 189:241–246 (1999)]. It seems a natural extension to apply this practice to lesions that are seen only with MRI, but can be targeted for ultrasound by using semiclotted blood. The intraoperative localization rate of 100% (19/19) has shown this method to be quite successful in the hands of surgeons experienced in the use of ultrasound.

This method of hematoma injection to mark breast lesions for removal also addresses many of the problems related to the standard practice for biopsy of nonpalpable lesions. The method avoids the discomfort of long-term needle placement in the breast. The actual MRI and localization procedure takes only about 45 minutes to an hour to perform. The breast lesion may be localized about several weeks before the surgical excision, thus lessening the need to coordinate the localization procedure in radiology with the surgical excision in the operating room. In the present study, the longest time from hematoma injection to surgical excision was 6 days. It is contemplated that this period can be extended by several weeks. Ultrasound-guided excisional breast biopsy was performed using stereotactically-induced hematomas to guide the dissection up to 3 weeks after the needle biopsy. The length of time between localization and excision would be limited by the amount of time it takes for the injected hematoma to reabsorb into the surrounding tissues. This allows a great deal of flexibility in scheduling, because the lesion may be localized at any time during the week before surgery. Problems such as wire migration and transection, which may occur with standard NLBB, are not an issue with hematoma-directed breast biopsy. In the initial patients in whom a needle was placed in addition to the hematoma, it was found that the hematoma more accurately represented the location of the lesion in the breast. The wire/needle had often migrated in the breast before the excision.

II. Hematoma Produced by SCNBB Methods

A. Patients 20 patients received SCNBB followed by ultrasound-guided excisional breast biopsy at the Arkansas Cancer Research Center. Lesions that revealed a pathologic diagnosis of cancer, a risk of associated carcinoma (e.g. atypia), or that were discordantly benign with a suspicious mammogram were surgically excised under ultrasound guidance. Ultrasound-guided excisions were performed by two staff breast surgeons and the breast surgical oncology fellow.

B. Stereotactic Biopsy and Ultrasound Localization

Figure 7:
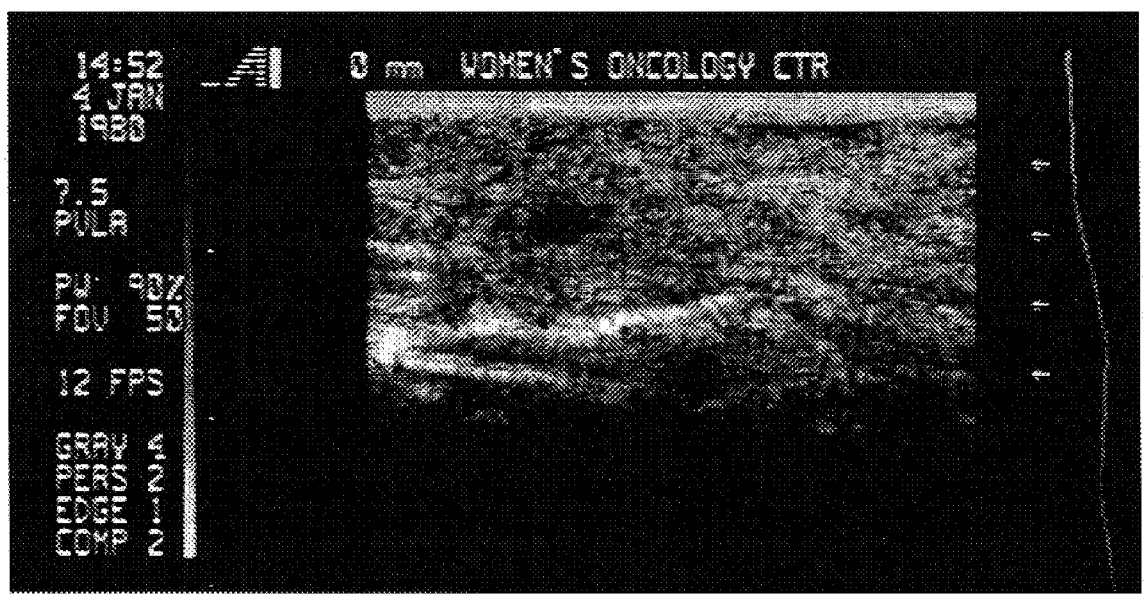
FIG. 7 represents a breast ultrasound showing hypoechoic hematoma with posterior shadowing resulting from SCNBB.

SCNBB was performed on patients in the prone position on a dedicated stereotactic table (Mammotest, Fisher Imaging, Denver, Colo.) using an 11-gauge vacuum-assisted Mammotome device (Biopsy Medical, Irvine, Calif.). Patients were then seen post-biopsy in the Women's Oncology Clinic several days after the SCNBB. At that time, a 7.5-MHz linear array transducer was used to assess the biopsy site in patients who would subsequently require surgical excision. The location and size of the hematoma were documented in the patient's record (FIG. 7). In a few of the early cases, the ultrasound-guided excision was scheduled with NLBB for back-up.

C. Intraoperative Ultrasound

Figure 8:
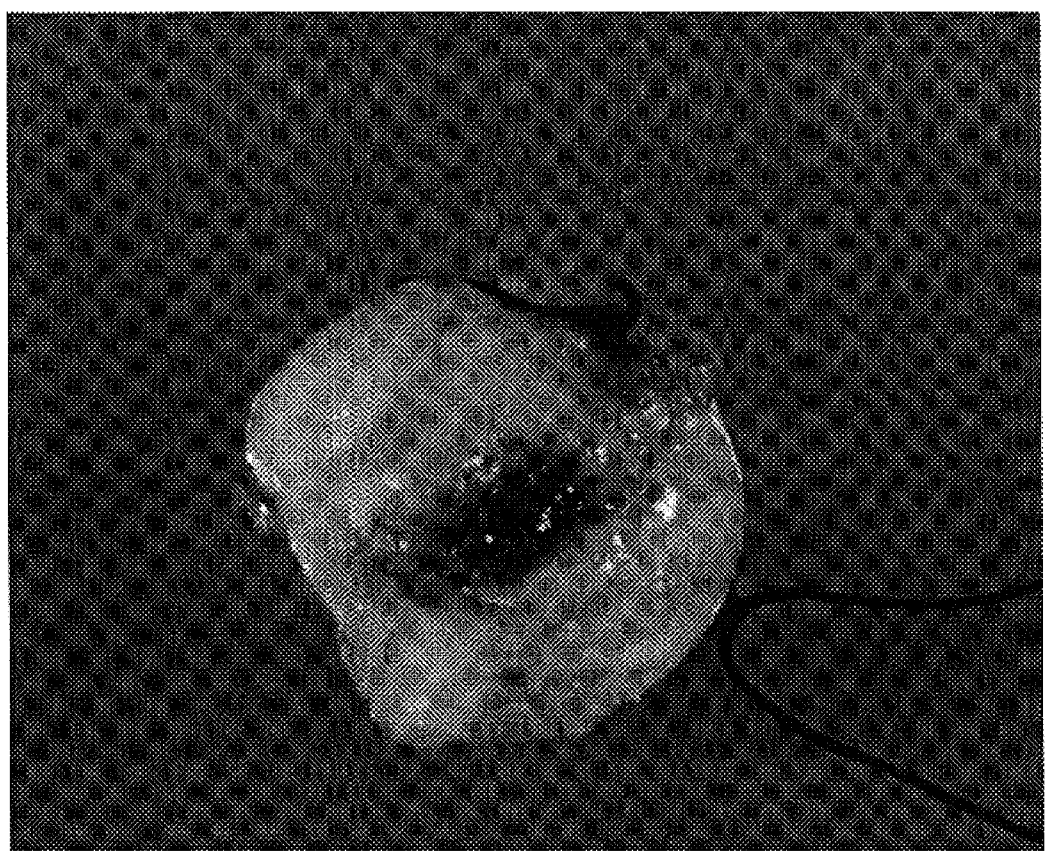
FIG. 8 is a gross breast specimen showing a hematoma resulting from SCNBB.
Figure 9:
FIG. 9 is a microscopic breast specimen demonstrating a hematoma resulting from SCNBB.

At the time of surgical excision, a sterilely covered 7.5-MHz linear array transducer (Acoustic Imaging, Dornier Medical Systems, Inc., Kenneshaw, Ga.) was used to determine the precise hematoma location within the breast. In those patients who also had NLBB, the lesion was localized on the morning of surgery in the radiology suite using a Homer MammaLok® Plus Needle (Medical Device Technologies, Inc., Gainesville, Fla.). When a needle was in place, the ultrasound probe was used to mark the skin incision overlying the lesion or needle tip. The resulting hematoma after SCNBB was localized in the standard longitudinal and transverse planes. After the incision was made, the transducer was placed inside the incision and the hematoma was again visualized. Dissection was carried straight down toward the chest wall using a "line of site" technique [Krag D et al., The sentinel node in breast cancer: a multicenter validation study, *New Engl J Med* 339:941–46 (1998)]. This technique was adapted from and mimics the use of the gamma probe in sentinel lymph node surgery. The transducer was placed perpendicular to the lesion and parallel to the chest wall to assess the adequacy of the deep margin. Tissue was excised around the hematoma in a block fashion down to the ascertained depth, aiming to achieve a 1-cm margin. Ex vivo ultrasound was performed on the specimen. Confirmation of excision of the targeted lesion was also determined by direct visualization of the hematoma in the gross specimen (FIG. 8) and microscopically (FIG. 9). Specimens were then sent to radiology, where specimen mammography also confirmed removal of the targeted lesion.

D. Pathology

Intraoperative touch prep cytology, which has been described by our institution and others [Klimberg V S et al., Use of touch preps for diagnosis and surgical margins in breast cancer, *Ann Surg Onc* 5(3):220–226 (1998); and Cox C E et al., Touch preparation cytology of breast lumpectomy margins with histologic correlation, *Arch Surg* 126:490–493 (1991)], was performed on all six margins (anterior, posterior, medial, lateral, superior, and inferior). Any margins positive by touch prep were re-excised. Subsequently, the margins were inked with six different colors for the six margins. Slides were stained with hematoxylin and eosin and examined for evidence of malignancy. The specimen was serially sectioned at 5-mm intervals. Permanent margins were classified as positive if tumor cells were present at the inked margin. Hematoxylin and eosin confirmed the removal of the hematoma and lesion.

Results

A. Patients

A total of 20 patients ranging in age from 41 to 77 years (average age, 56.6 years±10.1 years, SD) had mammographically detected lesions not visible on ultrasound. The majority of lesions (75%) were located in the upper outer quadrant of the breast. SCNBB was performed in these patients for suspicious or indeterminate microcalcifications [Brenner R J et al., Stereotactic core-needle breast biopsy: a multi-institutional prospective trial, Radiology. 218(3) :866–72 (2001)] or nodular densities [Snider H C et al., Intraoperative ultrasound localization of nonpalpable breast lesions, Ann Surg Onc 6(3):308–314 (1999)] on mammography. The average number of days from SCNBB to excision was 19 days±15 days, SD (range 4–56 days). All 20 patients had intraoperative US-guided excision of the previous SCNBB sites.

B. Stereotactic Biopsy and Ultrasound Localization

SCNBB was successful in 18 of the 20 patients included in the study. In one patient, SCNBB was aborted because it was felt not to be safe to proceed with biopsy due to the subarcolar position of the microcalcifications. However, the mammotome device was inserted into the breast while the patient was on the stereotactic table, and a hematoma was created. In a second patient, a specimen was taken, but the calcifications were inadequately sampled. Both of these patients had successful removal of the suspect area under ultrasound guidance.

NLBB as back up was scheduled when a prolonged period of time had elapsed between the SCNBB and excision or when it was early in the experience for the operating surgeon using this technique. 4 patients included in the study had a Homer MammaLok® needle placed for localization on the morning of surgery. At the time of surgery, ultrasound proved to be more accurate than needle localization for determining the lesion and appropriate incision location.

Ultrasound localization of the post-SCNBB hematomas was successful in 19 of 20 cases. In one patient with upper outer quadrant microcalcifications, a small hematoma was seen after SCNBB which revealed atypical ductal hyperplasia (ADH). At the time of surgery 9 days later, the surgeon had some difficulty localizing the hematoma by ultrasound. Specimen mammography was performed, but it did not show excision of the clip. Excision of an additional lateral margin resulted in removal of the clip and previous biopsy site. Although the appropriate area was entirely sampled and localized under ultrasound guidance, a specimen mammogram and excision of additional tissue was required to satisfactorily document successful removal of the targeted tissue.

C. Stereotactic Biopsy Pathology

All 19 SCNBB specimens were sent for permanent hematoxylin and eosin sections. Slides were reviewed at a weekly multidisciplinary breast conference with the pathologist. SCNBB pathology indicated that one patient had infiltrating mammary carcinoma and 2 patients had ductal carcinoma insitu (DCIS). SCNBB showed the remaining patients to have atypical lobular hyperplasia (ALH) (4), ADH (3), radial scar (2), papillomas (3), a mucinous lesion (1), tumoral adenosis (1), and discordant pathology with mammographic findings (2). One patient had an aborted SCNBB, as described previously, and did not have preoperative pathology results.

D. Excisional Biopsy Pathology

Excisional biopsy showed 3 (15%) of the excised lesions were malignant, with an average tumor size of 16 mm±14 mm, SD (range 5–32 mm). The average closest margin of patients undergoing lumpectomy only was 12 mm±7 mm, SD (range 7–20 mm). 2 (10%) lesions were LCIS. The benign lesions (15/20) comprised papillomas (3), radial scar (2), fibroadenoma (1), adenomyoepithelioma (1), and areas of sclerosing adenosis/ductal hyperplasia (8). 2 of the 7 patients with atypical hyperplasia on SCNBB were found to have lobular carcinoma insitu (LCIS) at excision. No additional cancers or areas of atypical hyperplasia were found at definitive excision. The hematoma visualized by ultrasound, and then grossly at surgery, could also be seen microscopically to again confirm lesion removal.

E. Complications 2 patients developed small postoperative hematomas that did not require surgery and subsequently resolved.

Discussion

The results demonstrate the effectiveness of intraoperative ultrasound in localizing post-SCNBB hematomas for excision. The technique of using intraoperative ultrasound for excision of previous SCNBB sites is an extension of a study which demonstrated the success of intraoperative ultrasound for localization and excision of echogenic lesions [Smith L F et al., Intraoperative ultrasound-guided breast biopsy, Am J Surg 180:419–423 (2000)].

SCNBB is at present primarily used as a diagnostic tool. Since it was first described by Parker [Parker S H et al., Stereotactic breast biopsy with a biopsy gun, Radiology 176:741–47 (1990)], this technique has proven successful in being less invasive and less expensive than NLBB while having an accuracy approaching 100% in the diagnosis of breast pathology [Velanovich F et al., Comprison of mammographically guided breast biopsy techniques, Ann Surg 229(5):625–33; Fuhrman G M et al., Image-guided core-needle breast biopsy is an accurate technique to evaluate patients with nonpalpable imaging abnormalities, Ann Surg 227(6):932–39 (1998); Meyer J E et al., Large-core needle biopsy of nonpalpable breast lesions, JAMA 281(17):1638–41 (1999); Howisey R L et al., A comparison of medicare reimbursement and results for various imaging-guided breast biopsy techniques, Am J Surg 173:395–398 (1997); Pettine S et al., Stereotactic breast biopsy is accurate, minimally invasive, and cost effective, Am J Surg 171:474–76 (1996); and Brenner R J et al., Stereotactic core-needle breast biopsy: a multi-institutional prospective trial, Radiology 218(3):866–72 (2001)]. Cost savings may be as great as 50% when compared to NLBB [Meyer J E et al., Large-core needle biopsy of nonpalpable breast lesions, JAMA 281(17):1638–41 (1999); Lee C H et al., Cost-effectiveness of stereotactic core needle biopsy: analysis by means of mammographic findings, Radiology 202:849–854 (1997); and Liberman L et al., Impact of stereotaxic core breast biopsy on cost of diagnosis, Radiology 195:633–637 (1995)]. However, in lesions requiring diagnostic excision after SCNBB, NLBB has been the only tool available for the localization and treatment of breast disease.

SCNBB must be followed by NLBB for known cancers, for definitive diagnosis when atypia is found, or when mammography and pathology are discordant [Bassett L et al., Stereotactic core needle biopsy of the breast: a report of the joint task force of the American College of Radiology, American College of Surgeons, and College of American Pathologists, CA Cancer J Clin. 47(3);171–90 (1997)]. Unfortunately, a significant number of patients suffer problems in association with NLBB, including a miss rate ranging from 0 to as high as 22% [Rissanen T J et al., Wire localized biopsy of breast lesions: a review of 425 cases found in screening or clinical mammography, Clin Radiol 47:14–22 (1993); Hasselgren P O et al., Breast biopsy with needle localization: accuracy of specimen x-ray and management of missed lesions, Surgery 114:836–42 (1993); and Homer M J et al., Prebiopsy needle localization: methods, problems, and expected results, Radiol Clin North Am 30(1):139–153 (1992)]; the possibility of wire transection, migration or dislocation; [[Rissanen T J et al., Wire localized biopsy of breast lesions: a review of 425 cases found in screening or clinical mammography, Clin Radiol 47:14–22 (1993); and Homer M J et al., Prebiopsy needle localization: methods, problems, and expected results, Radiol Clin North Am 30(1):139–153 (1992)]; scheduling difficulties; vasovagal reactions in up to 20%; and the discomfort of having a wire or needle in the breast while the patient is awaiting surgery.

With the current emphasis on increased screening mammography, a surgeon is often faced with the excision of nonpalpable breast lesions. Frequently, the surgeon has a tissue diagnosis from prior SCNBB, but the pathology or mammography findings dictate an excisional biopsy to excise malignancy or prove benignity. Preoperative SCNBB provides a tissue diagnosis and allows the surgeon to plan a definitive surgery that may include sentinel lymph node biopsy. The same SCNBB procedure also serves as a localizing technique.

This technique has many advantages over NLBB. It eliminates the need for an additional procedure, namely placement of a localizing wire or needle, which may pose a risk of complication and additional cost to the patient. The patient is much more comfortable because no preoperative wire is in place. Also, scheduling is made simpler. The surgeon need only schedule time in the operating room for the patient, without the requirement for the patient to go to radiology preoperatively. In these studies, the time from SCNBB to surgery was as long as 56 days. However, when the surgery is postponed for longer than one month after the SCNBB, the surgeon may wish to assess the breast with ultrasound just prior to the excision to document persistence of the hematoma. Unlike recent reports of radioguided occult lesion localization [Luini A et al., Comparison of radioguided excision with wire localization of occult breast lesions, Br J Surg 86(4):522–25 (1999); and Gennari R et al., Use of technetium-99m-labeled colloid albumin for preoperative and intraoperative localization of nonpalpable breast lesions, J Am Coll Surg 190:692–699 (2000)], this technique does not rely on the injection of any additional material into the breast or a second procedure. It allows the original diagnostic SCNBB to act as the localizing procedure for surgical excision. Although this technique can be readily applied to nonpalpable lesions, it does shift the onus of localization from the radiologist to the surgeon in that the surgeon must be experienced with the use of intraoperative ultrasound. One may initially wish to have a needle in the breast for backup while using the ultrasound to locate the post-SCNBB hematoma.

In conclusion, the methods of the present invention represent the introduction of a new technique of hematoma-directed ultrasound guided excisional breast biopsy. Currently, there is no injectable agent approved by the U.S. Food & Drug Administration (FDA) that can be imaged by ultrasound. Unlike other techniques under development, the procedure of the present invention does not require FDA approval because it uses the patient's own blood. This technique can be used not only to localize a MRI-detected lesion, but also to outline the targeted lesion for complete excision and to obtain margins. Although this technique can be readily applied to nonpalpable lesions (MRI or mammographic), it shifts the onus of localization from the radiologist to the surgeon in that the surgeon must be skilled in the use of intraoperative ultrasound.

All references referred to herein are hereby incorporated by reference in their entirety.

It should be understood that various changes and modifications to the presently preferred embodiments described herein will be apparent to those skilled in the art. Such changes and modifications can be made without departing from the spirit and scope of the present invention and without diminishing its attendant advantages.

We claim:

1. A method for detecting and excising nonpalpable lesions, comprising the steps of:
   (a) injecting at least one hematoma into a mammal's breast to mark a nonpalpable lesion; wherein the hematoma comprises approximately 2 ml to about 5 ml of the mammal's own blood;
   (b) detecting the location of the marked lesion using MRI; and thereafter
   (c) excising the marked lesion.

2. The method according to claim 1, further including step (d) of confirming the excision of the lesion by ex vivo ultrasound.

3. The method according to claim 1, wherein the hematoma is placed in the mammal's breast for a period of about several hours to about several days before excision of the marked lesion.

4. The method according to claim 1, further including the step of injecting the mammal's blood into a needle directed into the mammal's breast.

5. The method according to claim 1, further including the step of using intraoperative ultrasound to guide the excision of the marked lesion.

6. The method according to claim 1, wherein the marked lesion includes malignant lesions, papillomas, sclerosing adenosis, radial scars, fibroadenomas, and areas of atypical ductal hyperplasia.

7. The method according to claim 1, wherein the mammal is a human or animal.

8. The method according to claim 1, wherein the hematoma is in a mixture comprising at least one composition.

9. A method for detecting and excising nonpalpable lesions, comprising the steps of:
   (a) producing at least one hematoma in a mammal's breast by stereotactic core needle biopsy to mark a nonpalpable lesion;
   (b) detecting the location of the marked lesion using ultrasound; and thereafter
   (c) excising the marked lesion.

10. The method according to claim 9, wherein the marked lesion includes infiltrating mammary carcinomas, DCIS, ALH, ADH, papillomas, radial scars, fibroadenomas, adenomyepitheliomas, and areas of sclerosing adenosis/ductal hyperplasia.

11. The method according to claim 9, wherein the mammal is a human or an animal.

12. The method according to claim 9, wherein the ultrasound is performed intraoperatively.

13. The method according to claim 9, wherein the excision of the marked lesion is performed several hours to about 20 weeks after the SCNBB.

14. A method for marking nonpalpable lesions or obtaining the margins of the lesions, comprising the steps of:
   (a) injecting at least one hematoma into a mammal's breast to mark a nonpalpable lesion; wherein the hematoma comprises approximately 2 ml to about 5 ml of the mammal's own blood; and thereafter
   (b) detecting the location of the marked lesion or margins of the lesion using MRI.

15. The method according to claim 14, further including the step of injecting the mammal's blood into a needle directed into the mammal's breast.

16. The method according to claim 14, wherein the marked lesion includes malignant lesions, papillomas, sclerosing adenosis, radial scars, fibroadenomas, and areas of atypical ductal hyperplasia.

17. The method according to claim 14, wherein the mammal is a human or an animal.

18. A method for detecting and excising nonpalpable lesions, comprising the steps of:
   (a) injecting at least one hematoma into a pre-selected area in a mammal to mark a nonpalpable lesion; wherein the hematoma comprises approximately 2 ml to about 5 ml of the mammal's own blood;
   (b) detecting the location of the mark lesion using MRI; and thereafter
   (c) excising the mark lesion.

19. The method according to claim 18, further including step (d) of confirming the excision of the lesion by ex vivo ultrasound.

20. The method according to claim 18, wherein the hematoma is placed in the pre-selected area in the mammal for a period of about several hours to about several weeks before excision of the marked lesion.

21. The method according to claim 18, further including the step of injecting the mammal's blood into a needle directed into the pre-selected area in the mammal.

22. The method according to claim 18, further including the step of using intraoperative ultrasound to guide the excision of the marked lesion.

23. The method according to claim 18, wherein the mammal is a human or an animal.

24. The method according to claim 18, wherein the pre-selected area is any organ.

* * * * *

UNITED STATES PATENT AND TRADEMARK OFFICE
CERTIFICATE OF CORRECTION

PATENT NO. : 6,714,808 B1
DATED : March, 30, 2004
INVENTOR(S) : Kimberg et al.

It is certified that error appears in the above-identified patent and that said Letters Patent is hereby corrected as shown below:

Title page,
Item [73], Assignee, "University of Arkansas" should read -- Board of Trustees of the University of Arkansas --
Item [57], ABSTRACT,
Line, 3, "inventon" should read -- invention --

Column 12,
Lines 36 and 38, the word "mark" should read -- marked --

Signed and Sealed this

Eighth Day of March, 2005

JON W. DUDAS
*Director of the United States Patent and Trademark Office*